（12) United States Patent
Kamath et al.

(10) Patent No.: US 9,481,864 B1
(45) Date of Patent: Nov. 1, 2016

(54) CONVERSION OF NON-NEURONAL CELLS INTO NEURONS

(71) Applicants: Siddharth G. Kamath, Tampa, FL (US); Chad Dickey, Tampa, FL (US); Basil Cherpelis, Tampa, FL (US)

(72) Inventors: Siddharth G. Kamath, Tampa, FL (US); Chad Dickey, Tampa, FL (US); Basil Cherpelis, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 14/788,045

(22) Filed: Jun. 30, 2015

(51) Int. Cl.
| | |
|---|---|
| C12N 15/00 | (2006.01) |
| C12P 21/06 | (2006.01) |
| A61K 48/00 | (2006.01) |
| C12N 15/11 | (2006.01) |
| C12N 5/0793 | (2010.01) |
| C12N 15/65 | (2006.01) |
| C12N 15/113 | (2010.01) |
| A61K 35/30 | (2015.01) |

(52) U.S. Cl.
CPC ............ *C12N 5/0619* (2013.01); *A61K 35/30* (2013.01); *C12N 15/113* (2013.01); *C12N 15/65* (2013.01); *C12N 2310/122* (2013.01); *C12N 2506/1307* (2013.01)

(58) Field of Classification Search
None
See application file for complete search history.

(56) References Cited

U.S. PATENT DOCUMENTS

| 2011/0041857 A1 | 2/2011 | Schuldt et al. |
| 2013/0022583 A1 | 1/2013 | Wernig et al. |

FOREIGN PATENT DOCUMENTS

| WO | WO 2012/118988 | 9/2012 |
| WO | WO 2014/071157 | 5/2014 |

OTHER PUBLICATIONS

Blanchard, J. et al. "Selective conversion of fibroblasts into peripheral sensory neurons" *Nature Neuroscience*, 2015, 18(1):25-37.
Caiazzo, M. et al. "Direct generation of functional dopaminergic neurons from mouse and human fibroblasts" *Nature*, 2011, 476:224-229.
Hu, B-Y. et al. "Neural differentiation of human induced pluripotent stem cells follows developmental principles but with variable potency" *PNAS*, 2010, 107(9):4335-4340.
Patton, J.G. et al. "Characterization and Molecular Cloning of Polypyrimidine Tract-binding Protein: A Component of a Complex Necessary for Pre-mRNA Splicing" *Genes & Dev.*, 1991, vol. 5, No. 7, pp. 1237-1251.
Pfisterer, U. et al. "Direct conversion of human fibroblasts to dopaminergic neurons" *PNAS*, 2011, 108(25):10343-10348.
Son, E. et al. "Conversion of Mouse and Human Fibroblasts into Functional Spinal Motor Neurons" *Cell Stem Cell*, 2011, 9:205-218.
Theka, I. et al. "Rapid Generation of Functional Dopaminergic Neurons From Human Induced Pluripotent Stem Cells Through a Single-Step Procedure Using Cell Lineage Transcription Factors" *Stem Cells Trans. Med.*, 2013, 2:473-479.
Wattanapanitch, M. et al. "Dual small-molecule targeting of SMAD signaling stimulates human induced pluripotent stem cells toward neural lineages" *PLOS ONE*, 2014, 9(9):e106952 (8 pages).
Xue, Y. et al. "Direct Conversion of Fibroblasts to Neurons by Reprogramming PTB-Regulated MicroRNA Circuits" *Cell*, 2013, vol. 152, pp. 82-96.
Yoo, A. et al. "MicroRNA-mediated conversion of human fibroblasts to neurons" *Nature*, 2011, 476:228-232.
Xue, Z.W. et al. "Rho-associated coiled kinase inhibitor Y-27632 promotes neuronal-like differentiation of adult human adipose tissue-derived stem cells," *Chinese Medical Journal*, Sep. 2012, vol. 125, No. 18, pp. 3332-3335, Abstract.

*Primary Examiner* — Robert M Kelly
(74) *Attorney, Agent, or Firm* — Saliwanchik, Lloyd & Eisenschenk

(57) ABSTRACT

The subject invention concerns materials and methods for conversion of non-neuronal cells into neurons. The subject invention also concerns methods for screening drugs and other compounds for activity in treating Alzheimer's disease using neuronal cells produced using the subject invention. The subject invention also concerns neuronal cells that have been produced using the methods of the invention. The subject invention also concerns methods for evaluating therapeutic treatment for efficacy in a person or animal having Alzheimer's disease or other neurodegenerative diseases. The subject invention also concerns methods of treating Alzheimer's disease or other neurodegenerative diseases or conditions in a person or animal.

23 Claims, 5 Drawing Sheets
(4 of 5 Drawing Sheet(s) Filed in Color)

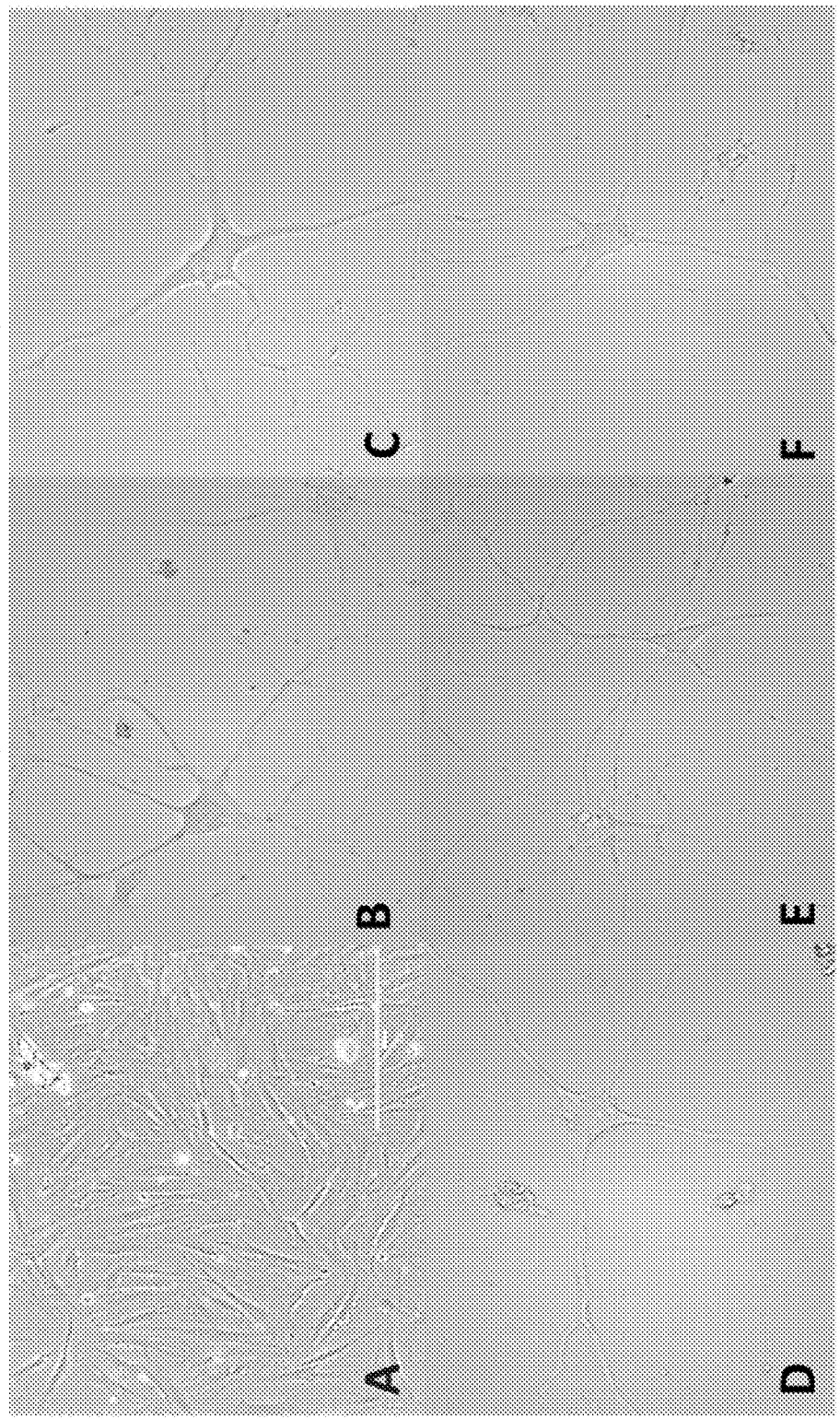

FIG. 3B
FIG. 3E
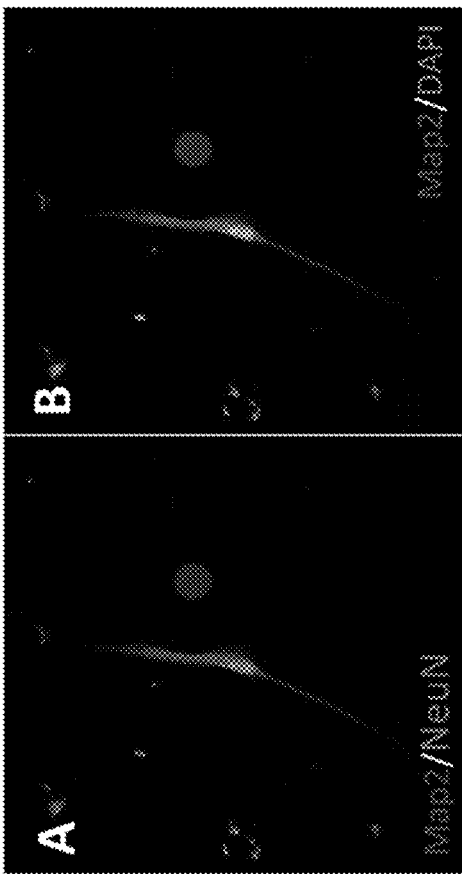
FIG. 3A
FIG. 3C
FIG. 3D

FIG. 4A
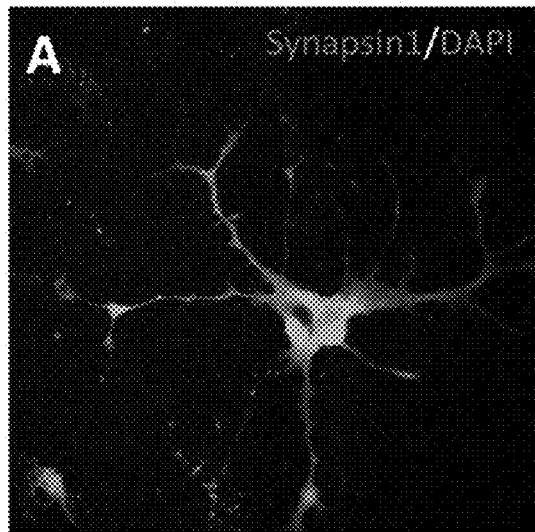
FIG. 4B
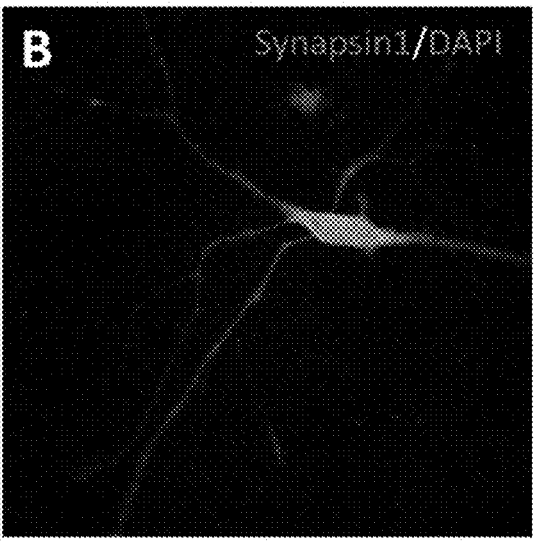
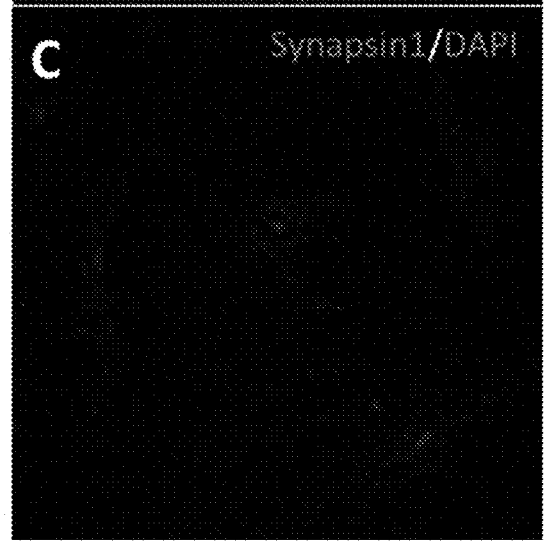
FIG. 4C

CONVERSION OF NON-NEURONAL CELLS INTO NEURONS

BACKGROUND OF THE INVENTION

Alzheimer's disease (AD) is most common cause of dementia amongst people over 65 years old (National Institute of Aging). Increasing evidence suggests that multifactorial events occur between the initial phases of the disease and the end stage pathology. One of the most common proteins in AD pathology is a Tau, a soluble, microtubule-associated protein known to aberrantly form amyloid-positive aggregates. Therefore, developing an ex vivo assay to screen drugs using individual patient cells to slow or diminish these aggregates would be helpful in discovering new therapies for AD. Recent advances in stem cell research have rekindled newer ways of synthesizing the cells of interest using lineage-specific transcription factors. This process of cell conversion takes longer time because of the generation of iPSCs (induced pluripotent stem cells) first, followed by differentiation of iPSCs into cells of interest. A group from UCSD recently has developed a direct conversion method to obtain neurons from fibroblast without the step of first generating iPSCs (Xue, 2013). This method has shortened the time course of neuron development, but it still takes 19 days post antibiotic selection and requires expensive neurotrophic factors. Here we have developed a modified protocol to convert fibroblasts into neurons using readily available medium from vendors. In addition to the lower cost, we have also seen reduction in time (6-8 days post selection) to obtain induced neurons in culture.

BRIEF SUMMARY OF THE INVENTION

The subject invention concerns materials and methods for conversion of non-neuronal cells into neurons. The subject invention also concerns methods for screening drugs and other compounds for activity in treating Alzheimer's disease using neuronal cells produced using the subject invention. The subject invention also concerns neuronal cells that have been produced using the methods of the invention. The subject invention also concerns methods for evaluating therapeutic treatment for efficacy in a person or animal having Alzheimer's disease or other neurodegenerative diseases. The subject invention also concerns methods of treating Alzheimer's disease or other neurodegenerative diseases or conditions in a person or animal.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

FIGS. 1A-1F: Live cell imaging using Cytation3 reader (BioTek). (FIG. 1A) day 1 cultured fibroblast from skin biopsy; (FIGS. 1B-1F) cells that received PTB1_Hygromycin transduction after 8-10 days post hygromycin selection (in Neural induction medium containing 10 µM Rock inhibitor).

FIGS. 3A-3E: After 8-10 days when cells started showing neuron-like morphology (FIGS. 3A-3D: PTB1-shRNA and FIG. 3E: Ctrl-shRNA), they were fixed with 4% PFA and first stained with the primary antibodies, anti-mouse NeuN and anti-rabbit MAP2. The secondary antibody used was Alexa-488 (mouse) and Alexa-594 (Rabbit) for immunofluorescence. The nuclei were counterstained with DAPI.

FIGS. 4A-4C: After 8-10 days when cells started showing neuron-like morphology (FIGS. 4A and 4B: PTB1-shRNA and FIG. 4C: Ctrl-shRNA), they were fixed with 4% PFA and first stained with the primary antibodies, anti-mouse Synapsin1. The secondary antibody used was Alexa-488 (mouse) for immunofluorescence. The nuclei were counterstained with DAPI.

BRIEF DESCRIPTION OF THE SEQUENCES

Figures 2A, 2B, 2C, 2D, 2E:
FIGS. 2A-2E: After 8-10 days when cells started showing neuron-like morphology (FIGS. 2A-2D: PTB1-shRNA and FIG. 2E: Ctrl-shRNA) they were fixed with 4% PFA and first stained with the primary antibodies, anti-mouse neuron-specific β-Tubulin and anti-rabbit PTB1. The secondary antibody used was Alexa-488 (mouse) and Alexa-594 (Rabbit) for immunofluorescence. The nuclei were counterstained with DAPI.

SEQ ID NOs:1-4 are the mature antisense sequences of a PTB protein shRNA that can be used with the present invention to inhibit PTB expression.

DETAILED DESCRIPTION OF THE INVENTION

The subject invention concerns materials and methods for conversion of non-neuronal cells into neurons. In one embodiment, a method of the invention comprises inducing conversion of a non-neuronal cell to a neuronal cell, comprising the steps of i) incorporating into the non-neuronal cell a polynucleotide of polypyrimidine-tract-binding (PTB) protein short hairpin RNA (shRNA) that silences or inhibits PTB expression and a polynucleotide encoding a selectable marker and expressing said polynucleotide in said non-neuronal cell; ii) selecting for a cell expressing said selectable marker; and iii) culturing the selected cell in a neural induction medium comprising a ROCK inhibitor for a sufficient period of time to induce neuronal development, whereby the selected cell is converted into a neuronal cell. In a specific embodiment, the non-neuronal cell is a fibroblast. In one embodiment, prior to incorporating the polynucleotide into the non-neuronal cell, the cells can be cultured on a substrate, typically for several hours. In a specific embodiment, the substrate is coated with poly-D-lysine and laminin. Following this culture, the cells are treated in a manner to incorporate into the cell a polynucleotide of polypyrimidine-tract-binding (PTB) protein short hairpin RNA (shRNA) and a polynucleotide encoding for a selectable marker, such as antibiotic resistance. Any shRNA that targets and silences or inhibits expression of PTB in the cell is contemplated within the scope of the invention. Sequences of genes encoding PTB protein are known in the art (e.g., Genbank Accession No. X60648.1). Polynucleotides can be incorporated into the cell using any suitable methods in the art. In one embodiment, cells are transduced using a virus or viral vector. Any suitable virus or vector is contemplated within the scope of the invention. In one embodiment, cells are cultured in a medium comprising the polynucleotide that facilitates incorporation of the polynucleotide into the cells. Examples of viruses that can be used include, but are not limited to, adenovirus, adeno-associated virus (AAV), retrovirus, and lentivirus. In a specific embodiment, the virus is a lentivirus. Methods for viral transduction of cells are known in the art. In a specific embodiment, the transduction proceeds for about 16 hours. Following incorporation of the polynucleotide in the cell, the culture medium can be replaced with fresh medium (lacking the polynucleotide) and cells cultured for several hours. Cells that express the incorporated polynucleotide are then selected by selecting for those cells that express the selectable marker. In one embodiment, the selectable marker provides for antibiotic resistance and the cells are selected by exposure to the antibiotic, such as hygromycin. Antibiotic selection can proceed for several hours, typically about 48 hours.

Following selection of cells expressing the selectable marker, the selected cells are cultured in a neural induction medium comprising a rho-associated kinase (ROCK) inhibitor. In one embodiment, the ROCK inhibitor is the inhibitor designated as Y-27632 and having the structure:

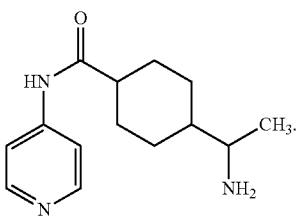 [SMILES: CC(N)C1CCC(C(=O)Nc2ccncc2)CC1]

Other ROCK inhibitors contemplated within the scope of the present invention include, but are not limited to,

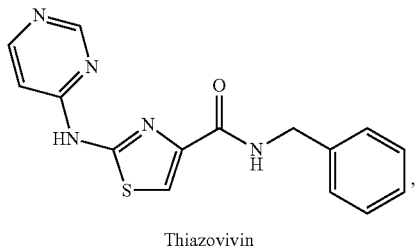

Thiazovivin

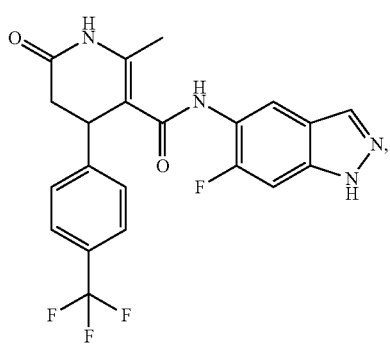

GSK429286A

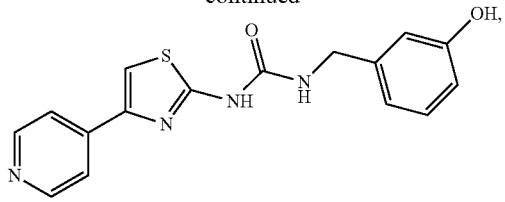

RKI-1447

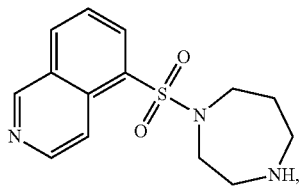

Fasudil (HA-1077)

and

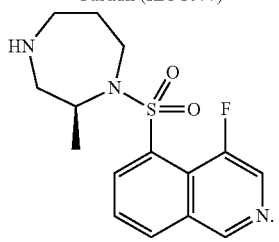

Ripasudil

The cells are cultured in the presence of the ROCK inhibitor for a sufficient period of time to induce neuronal development. In one embodiment, the cells are cultured in the ROCK inhibitor for from a few days to several days. In a specific embodiment, the cells are cultured in the presence of the ROCK inhibitor for about 48 hours. The neural induction medium can be replaced one or more times during the time period for induction of the cells into neurons. Following culture with the ROCK inhibitor, the cells can optionally be cultured in the medium without the ROCK inhibitor for several hours to several days. Cells can be monitored for conversion to a neuronal phenotype, e.g., suing antibodies that bind to neuron-associated markers. In a specific embodiment, the cell expresses neuron-associated markers, such as β-tubulin, NeuN, microtubule-associated protein 2 (MAP2), and/or Synapsin1. Following conversion to neuronal phenotype, neuronal cells can be removed from the ROCK inhibitor and cultured as appropriate in a suitable culture medium and under suitable growth conditions.

In one embodiment, the non-neuronal cells of the invention are non-neuronal somatic cells. In a specific embodiment, the cells are mammalian cells. In a more specific embodiment, the non-neuronal cells are human cells. The non-neuronal cells can be cells that have been cultured in vitro, or cells that are freshly isolated from an animal. In one embodiment, the cells are epithelial cells. In a specific embodiment, the cells are fibroblasts, melanocytes, keratinocytes, adipocytes, or Langerhans cells. Methods for preparing various non-neuronal cell types are known in the art. The non-neuronal cells can be obtained from a person or animal by invasive or non-invasive means. In one embodiment, cells are obtained by way of a biopsy, e.g., a skin biopsy. The non-neuronal cells can be from a patient having a neurodegenerative disease or condition. In a specific embodiment, the non-neuronal cells are fibroblasts and can be obtained from any suitable tissue such as skin (dermis), foreskin, lung, etc. The neuronal cells of the invention can be any type of cell of the nervous system. In one embodiment, the neuron is a motor neuron. In another embodiment, the neuron is a sensory neuron. In a further embodiment, the neuron is an inter-neuron. In one embodiment, the induced neurons are able to uptake monomeric Tau protein into the cell.

The subject invention also concerns neuronal cells that have been produced using the methods of the invention. The neuronal cells can be produced from cells of the person or animal that is to receive the neuronal cells (e.g., via implantation) or the person or animal who is to be evaluated for potential efficacy of a therapeutic treatment. In one embodiment, the neuronal cell is a mammalian cell. In a specific embodiment, the neuronal cell is a human cell. In one embodiment, the cell expresses one or more neuron-associated markers, such as β-tubulin, NeuN, microtubule-associated protein 2 (MAP2), and/or Synapsin1.

The subject invention also concerns methods for screening drugs and other compounds for activity in treating Alzheimer's disease or other neurodegenerative diseases using neuronal cells produced using the subject invention. In one embodiment, neuronal cells produced by methods of the invention are used to screen for drugs or compounds that inhibit the formation of aggregates of Tau protein in the cells. In a specific embodiment, a method comprises contacting a neuronal cell of the invention with a test drug or compound, and evaluating whether the drug or compound inhibits the formation of aggregates of Tau protein in the cell relative to control cells or cells that were not contacted or relative to a pre-determined baseline level of Tau aggregation. Any method for measuring Tau aggregation is contemplated within the scope of the invention. In one embodiment, the cells are from the person or animal who may be treated with the drug or compound being screened. In one embodiment, the cell expresses one or more neuron-associated markers, such as β-tubulin, NeuN, microtubule-associated protein 2 (MAP2), and/or Synapsin1.

The subject invention also concerns methods for evaluating a therapeutic treatment for efficacy in a person or animal having Alzheimer's disease or another neurodegenerative disease. In one embodiment, cells are obtained from the person or animal. In a specific embodiment, the cells are fibroblasts from the person or animal. The cells are then converted into neuronal cells using the conversion methods of the present invention. The neuronal cells are then exposed to the therapeutic treatment being evaluated. The efficacy and impact of the therapeutic treatment on the cells can then be evaluated. In one embodiment, the converted neuronal cells are contacted with a drug or compound for use in treating the person or animal's disease, and the cells' response to the drug or compound is evaluated. In one embodiment, the ability of the drug or compound to inhibit the formation of aggregates of Tau protein in the converted neuronal cells is evaluated. If the therapeutic treatment evaluates as having efficacy with the converted neuronal cells, then the person or animal may be considered a candidate for the therapeutic treatment.

The subject invention also concerns methods of treating Alzheimer's disease or other neurodegenerative diseases or conditions in a person or animal. In one embodiment, a method of the invention comprises preparing a neuronal cell from a non-neuronal cell of the person or animal using the methods of the present invention, and subsequently administering or implanting the neuronal cell into the person or animal. In one embodiment, the neuronal cell is implanted into neural tissue of the person or animal. In a specific embodiment, the neuronal cell is administered or implanted into neural tissue (e.g., brain) of the person or animal.

Neurodegenerative diseases and conditions contemplated within the scope of the invention include, but are not limited to, Alzheimer's disease, Parkinson's disease, Huntington's disease, amyotrophic lateral sclerosis (ALS), stroke, spinal cord injury, gangliogliomas and gangliocytomas, argyrophilic grain dementia, corticobasal degeneration, dementia pugilistica, frontotemporal dementia with parkinsonism linked to chromosome17, Pick's disease, Hallervorden-Spatz disease, myotonic dystrophy, Niemann-Pick disease (type C), Parkinsonism-dementia complex of Guam, post-encephalitic parkinsonism, prion diseases (some), progressive subcortical gliosis, and progressive supranuclear palsy.

In vivo application of the subject converted neuronal cells, and compositions containing them, can be accomplished by any suitable method and technique presently or prospectively known to those skilled in the art. The subject cells can be formulated in a physiologically- or pharmaceutically-acceptable form and administered by any suitable route known in the art including, for example, oral, nasal, rectal, and parenteral routes of administration. In one embodiment, the subject cells can be administered by implantation, e.g., surgical implantation into the brain of a person or animal. As used herein, the term parenteral includes subcutaneous, intradermal, intravenous, intramuscular, intraperitoneal, and intrasternal administration, such as by injection. Administration of the subject cells of the invention can be a single administration, or at continuous or distinct intervals as can be readily determined by a person skilled in the art.

Mammalian species that benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo bison, horses, donkey, swine, sheep, and goats; exotic animals typically found in zoos such as bear, lions, tigers, panthers, elephants, hippopotamus, rhinoceros, giraffes antelopes, sloth, gazelles, zebras, wildebeests, prairie dogs, koala bears, kangaroo opossums, raccoons, pandas, hyena, seals, sea lions, elephant seals, otters, porpoises dolphins, and whales. As used herein, the terms "subject" "host", and "patient" are used interchangeably and intended to include such human and non-human mammalian species.

Materials and Methods

Antibodies Used for ICC

Polypyrimidine Tract Binding Protein1 (PTB1). These proteins are associated with pre-mRNAs in the nucleus and appear to influence pre-mRNA processing and other aspects of mRNA metabolism and transport.

Tubulin, Beta 3 Class III. Primarily expressed in neurons and may be involved in neurogenesis and axon guidance and maintenance.

MAP2. This gene encodes a protein that belongs to the microtubule-associated protein family. The proteins of this family are thought to be involved in microtubule assembly, which is an essential step in neurogenesis.

Synapsin1. This gene is a member of the synapsin gene family. Synapsins encode neuronal phosphoproteins which associate with the cytoplasmic surface of synaptic vesicles.

NeuN. A homologue to sex-determining genes in *C. elegans*, is a neuronal nuclear antigen that is commonly used as a biomarker for neurons.

Conversion of Adult Skin Fibroblasts into Induced-Neurons (I-NS)

1. 6 mm punch biopsy from adult arm is placed immediately into 15 ml tube containing DMEM with 1% pen-strep.
2. In cell culture hood, transfer the skin sample to the 15 ml conical tube containing 1 ml digestion medium (20% FBS+0.25% Collagenase type I+1% Pen-Strep in high glucose DMEM) and incubate at 37° C. overnight.
3. Next day, add 7 ml fibroblast culture medium (20% FBS+1% Pen-Strep in high glucose with sodium pyruvate plus L-glutamine) to the conical tube, pipette up and down for 2-3 times and then plate entire contents in a T75 tissue culture flask.
4. Incubate for 3 days without touching the flask.
5. On day 6-7, add 7 ml (Medium 1: 10% FBS+1% Pen-Strep in high glucose with sodium pyruvate), when cells are 80% confluent, passage 1:3 using 0.25% trypsin/EDTA.
6. Begin reprogramming at passage 3.
7. In 24-well plate, place a poly-d-lysine/Laminin coated coverslips (GG-12-15.5-Laminin, Neuvitro Corp.) and add 500 µl medium 1 to make sure to cover it. Add 9000 to 10,000 fibroblasts (from step 6) on the coverslip in 500 µl medium 1. Incubate overnight at 37° C. overnight.
8. Remove the medium and add 350 µl lentivirus particles containing PTB1 shRNA.
9. Incubate the cells at 37° C. for 16 hrs and replace the lentivirus particles with medium 1.
10. After 24 hrs, add medium 1 containing 100 µg/ml hygromycin to kill the cells that has not been transduced. Incubate for 24 to 48 hrs, depending on cell death.
11. Replace the medium with 350 µl STEMDIFF™ Neural Induction medium (StemCell Technologies) containing 10 µM Y-27632 (Rock inhibitor, StemCell Technologies).
12. Repeat step 11 again after 24 hrs.
13. After two cycles of Rock inhibitor treatment, add 350 µl STEMDIFF™ Neural Induction medium without Rock inhibitor for another 6-8 days until you see i-neurons.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Figure 5:
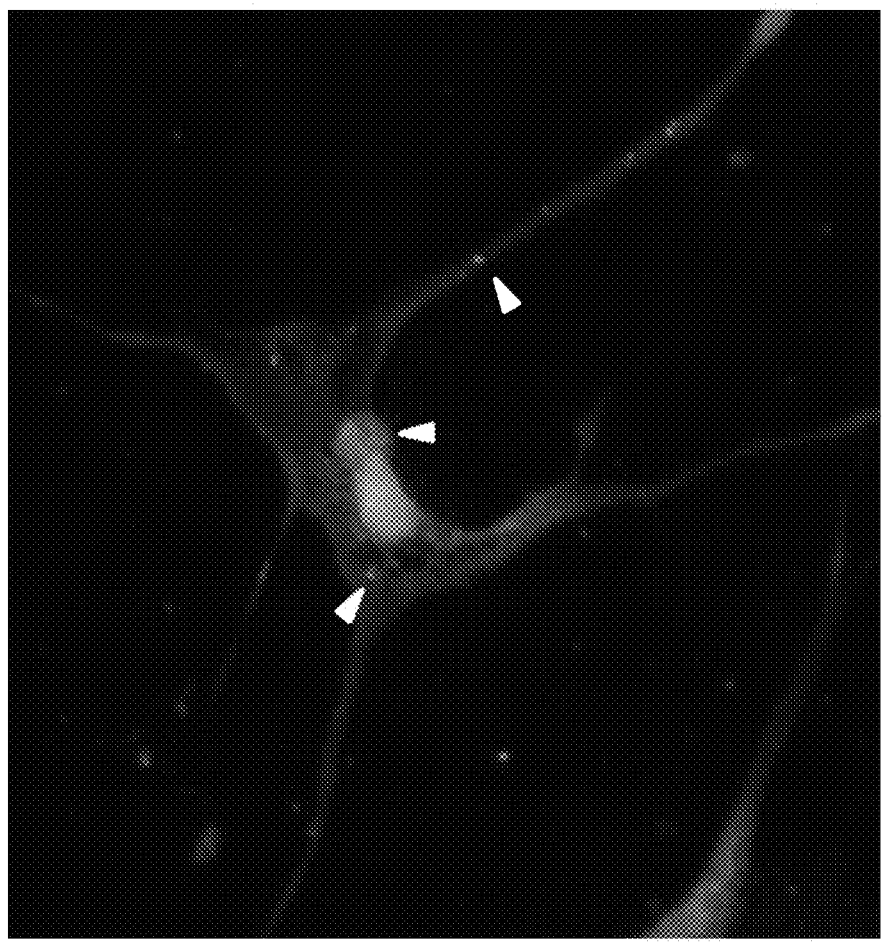
FIG. 5: Induced neurons of the invention incubated with 5 µM Alexa fluor-488 labeled Monomeric-Tau: Induced-Neurons were incubated with 5 uM Alexa fluor-488 labeled monomeric Tau for 24 hrs and washed with PBS several times. Tau aggregates are seen in neurites as well inside the cell (white arrowheads). The nucleus (blue) was DAPI stained.

Fibroblasts obtained from human skin are cultured on a coverslip coated with poly-D-lysine and laminin overnight. The following day, cells are transduced with lentivirus containing PTB1 shRNA for 16 hours and the medium is replaced. After 24 hours, the cells are selected using hygromycin (100 ng/ml) for 48 hours. The neural induction medium containing (10 µM) Rock inhibitor is added and cells are incubated for 6-8 days for induced neuronal development (see FIGS. 1-4). As shown in FIG. 5, the induced neurons are able to uptake monomeric Tau and form Tau aggregates inside the cell. In summary, we have successfully induced neurons from human skin fibroblast in half the time that is reported by others and without using any expensive neurotrophic factors. This newly discovered method will hasten personalized medicine approaches for Alzheimer's disease and possibly many other neurodegenerative diseases.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Xue, Y., Kunfu Ouyang, Jie Huang, Yu Zhou, Hong Ouyang, Hairi Li, Gang Wang et al. "Direct Conversion of Fibroblasts to Neurons by Reprogramming PTB-Regulated MicroRNA Circuits" *Cell*, 2013, 152:82-96.

Patton, J. G. et al. "Characterization and Molecular Cloning of Polypyrimidine Tract-binding Protein: A Component of a Complex Necessary for Pre-mRNA Splicing" *Genes Dev.*, 1991, 5(7):1237-1251.

We claim:

1. A method for inducing conversion of a non-neuronal cell to a neuronal cell, comprising:
   i) incorporating into said non-neuronal cell a polynucleotide, wherein said polynucleotide comprises a) a region that is or encodes a polypyrimidine-tract-binding (PTB) protein short hairpin RNA (shRNA) and b) a region that encodes a selectable marker;
   ii) selecting for a cell expressing said selectable marker;
   iii) culturing said selected cell in a neural induction medium comprising a ROCK inhibitor for a sufficient period of time to induce neuronal development, whereby said selected cell is converted into a neuronal cell.

2. The method according to claim 1, wherein said polynucleotide is incorporated into said non-neuronal cell using a virus or viral vector.

3. The method according to claim 2, wherein said virus or vector is adenovirus, AAV, retrovirus, or lentivirus.

4. The method according to claim 1, wherein said cell is a human cell.

5. The method according to claim 1, wherein said non-neuronal cell is a fibroblast cell.

6. The method according to claim 1, wherein said selectable marker is antibiotic resistance.

7. The method according to claim 1, wherein prior to step i), said non-neuronal cell is cultured on a substrate.

8. The method according to claim 7, wherein said substrate is coated with poly-D-lysine and/or laminin.

9. The method according to claim 1, wherein said ROCK inhibitor is a compound comprising a structure selected from:

Y-27632

Thiazovivin

GSK429286A

RKI-1447

Fasudil (HA-1077) or

-continued

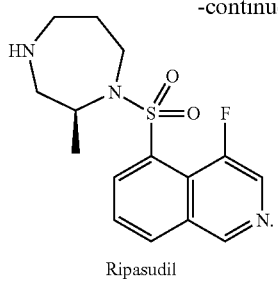

Ripasudil

10. The method according to claim 1, wherein said neuronal cell expresses one or more of tubulin, MAP2, synapsin, or NeuN.

11. The method according to claim 1, wherein said selected cell is cultured in said neural induction medium for about 48 hours.

12. The method according to claim 1, wherein said neural induction medium is replaced one or more times during said culturing period.

13. The method according to claim 1, wherein following said culturing period with said ROCK inhibitor, said selected cell is cultured in a medium without said ROCK inhibitor.

14. The method according to claim 1, wherein said non-neuronal cell is a somatic cell.

15. The method according to claim 1, wherein said non-neuronal cell is an epithelial cell.

16. The method according to claim 1, wherein said non-neuronal cell is from a person or animal having a neurodegenerative disease or condition.

17. The method according to claim 1, wherein said neuronal cell is capable of uptake of monomeric Tau protein into said neuronal cell.

18. The method according to claim 1, wherein said non-neuronal cell is a melanocyte, a keratinocyte, an adipocyte, or a Langerhans cell.

19. The method according to claim 16, wherein said neurodegenerative disease or condition is Alzheimer's disease, Parkinson's disease, Huntington's disease, amyotrophic lateral sclerosis (ALS), stroke, spinal cord injury, gangliogliomas and gangliocytomas, argyrophilic grain dementia, corticobasal degeneration, dementia pugilistica, frontotemporal dementia with parkinsonism linked to chromosome17, Pick's disease, Hallervorden-Spatz disease, myotonic dystrophy, Niemann-Pick disease (type C), Parkinsonism-dementia complex of Guam, postencephalitic parkinsonism, prion diseases, progressive subcortical gliosis, or progressive supranuclear palsy.

20. The method according to claim 1, wherein said non-neuronal cell is obtained via a biopsy of a person or animal.

21. The method according to claim 1, wherein said non-neuronal cell is obtained from skin, foreskin, lung, or dermal tissue.

22. The method according to claim 1, wherein said neuronal cell is a motor neuron, a sensory neuron, or an inter-neuron.

23. The method according to claim 1, wherein said ROCK inhibitor is

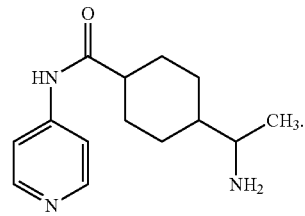

Y-27632

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Homo sapiens

<400> SEQUENCE: 1
attgttgtac ttgacgttga g                                              21

<210> SEQ ID NO 2
<211> LENGTH: 21
<212> TYPE: DNA
<213> ORGANISM: Homo sapiens

<400> SEQUENCE: 2
```

```
ttgctgtcat ttccgtttgc t                                              21

<210> SEQ ID NO 3
<211> LENGTH: 21
<212> TYPE: DNA
<213> ORGANISM: Homo sapiens

<400> SEQUENCE: 3
aacttgaatc ctttgacgac g                                              21

<210> SEQ ID NO 4
<211> LENGTH: 21
<212> TYPE: DNA
<213> ORGANISM: Homo sapiens

<400> SEQUENCE: 4
aactggatgt agatgggctg g                                              21
```